(12) United States Patent
Ostroff et al.

(10) Patent No.: US 9,042,980 B2
(45) Date of Patent: May 26, 2015

(54) SIGNAL ANALYSIS IN IMPLANTABLE CARDIAC TREATMENT DEVICES (75) Inventors: Alan H. Ostroff, San Clemente, CA (US); James W. Phillips, Fountain Valley, CA (US); Venugopal Allavatam, Oceanside, CA (US)

(73) Assignee: CAMERON HEALTH, INC., St. Paul, MN (US)

( * ) Notice: Subject to any disclaimer, the term of this patent is extended or adjusted under 35 U.S.C. 154(b) by 805 days.

(21) Appl. No.: 13/213,420

(22) Filed: Aug. 19, 2011

(65) Prior Publication Data

US 2011/0307024 A1 Dec. 15, 2011

Related U.S. Application Data

(62) Division of application No. 11/527,184, filed on Sep. 26, 2006, now Pat. No. 8,014,851.

(51) Int. Cl.
*A61B 5/0472* (2006.01)
*A61N 1/05* (2006.01)
*A61B 5/0452* (2006.01)
*A61B 5/0428* (2006.01)
*A61N 1/37* (2006.01)
*A61N 1/375* (2006.01)
*A61N 1/39* (2006.01)

(52) U.S. Cl.
CPC ............ *A61N 1/05* (2013.01); *A61B 5/04525* (2013.01); *A61B 5/0428* (2013.01); *A61B 5/0472* (2013.01); *A61B 5/0452* (2013.01); *A61N 1/0563* (2013.01); *A61N 1/3704* (2013.01); *A61N 1/3756* (2013.01); *A61N 1/3925* (2013.01); *A61N 1/3962* (2013.01)

(58) Field of Classification Search
None
See application file for complete search history.

(56) References Cited

U.S. PATENT DOCUMENTS

| 4,754,757 | A |   | 7/1988  | Feucht |
| 5,263,486 | A | * | 11/1993 | Jeffreys ..................... 600/508 |
| 5,513,644 | A | * | 5/1996  | McClure et al. ............ 600/521 |
| 5,836,982 | A | * | 11/1998 | Muhlenberg et al. ............ 607/9 |
| 6,275,786 | B1 |  | 8/2001  | Daners |
| 8,014,851 | B2 |  | 9/2011  | Ostroff et al. |
| 2002/0091333 | A1 | | 7/2002 | Hsu et al. |

(Continued)

FOREIGN PATENT DOCUMENTS

| CN | 101583397 B | 11/2013 |
| EP | 2077889 B1  | 7/2013  |

(Continued)

OTHER PUBLICATIONS

"U.S. Appl. No. 11/527,184, Non Final Office Action mailed May 27, 2010", 6 pgs.

(Continued)

*Primary Examiner* — Kennedy Schaetzle
(74) *Attorney, Agent, or Firm* — Seager, Tufte & Wickhem LLC (57) ABSTRACT

Methods and devices for cardiac signal analysis in implantable cardiac therapy systems. Several signal processing and/or conditioning methods are shown including R-wave detection embodiments including the use of thresholds related to previous peak amplitudes. Also, some embodiments include sample thresholding to remove extraneous data from sampled signals. Some embodiments include weighting certain samples more heavily than other samples within a sampled cardiac signal for analysis.

20 Claims, 9 Drawing Sheets

(56) References Cited

U.S. PATENT DOCUMENTS

| | | |
|---|---|---|
| 2003/0097153 A1 | 5/2003 | Bardy et al. |
| 2004/0059323 A1 | 3/2004 | Sturm et al. |
| 2004/0171953 A1 | 9/2004 | Hemming et al. |
| 2005/0101947 A1 | 5/2005 | Jarrard et al. |

FOREIGN PATENT DOCUMENTS

| | | |
|---|---|---|
| WO | 03-022356 A2 | 3/2003 |
| WO | WO-03022356 A2 | 3/2003 |
| WO | 2004-012596 A1 | 2/2004 |
| WO | WO-2005011809 A2 | 2/2005 |
| WO | WO-2005110263 A2 | 11/2005 |
| WO | WO-2008039841 A2 | 4/2008 |

OTHER PUBLICATIONS

"U.S. Appl. No. 11/527,184, Non Final Office Action mailed Nov. 26, 2010", 4 pgs.

"U.S. Appl. No. 11/527,184, Notice of Allowance mailed May 5, 2011", 5 pgs.

"U.S. Appl. No. 11/527,184, Response filed Feb. 28, 2011 to Non Final Office Action mailed Nov. 26, 2010", 6 pgs.

"U.S. Appl. No. 11/527,184, Response filed Aug. 27, 2010 to Non Final Office Action mailed May 27, 2010", 10 pgs.

"U.S. Appl. No. 11/527,184, Response filed Oct. 8, 2009 to Restriction Requirement mailed Sep. 8, 2009", 5 pgs.

"U.S. Appl. No. 11/527,184, Restriction Requirement mailed Sep. 8, 2009", 7 pgs.

"Australian Application Serial No. 2007300113, Office Action mailed Jan. 24, 2013", 3 pgs.

"Canadian Application Serial No. 2,663,756, Office Action mailed Nov. 18, 2013", 3 pgs.

"Chinese Application Serial No. 200780035483.7, Office Action mailed Jan. 18, 2013", With English Translation, 14 pgs.

"Chinese Application Serial No. 200780035483.7, Response filed Mar. 26, 2013 to Office Action mailed Jan. 18, 2013", With English Claims, 8 pgs.

"European Application Serial No. 07843228.3, Office Action mailed Feb. 26, 2010", 4 pgs.

"European Application Serial No. 07843228.3, Office Action mailed Jun. 29, 2012", 5 pgs.

"European Application Serial No. 07843228.3, Response filed Jun. 29, 2010 to Office Action mailed Feb. 26, 2010", 9 pgs.

"European Application Serial No. 07843228.3, Response filed Nov. 6, 2012 to Office Action mailed Jun. 29, 2012", 10 pgs.

"International Application Serial No. PCT/US2007/079535, International Preliminary Report on Patentability mailed Mar. 31, 2009", 7 pgs.

"International Application Serial No. PCT/US2007/079535, Written Opinion mailed May 7, 2008", 6 pgs.

Office Action (dated Nov. 25, 2010) and Applicant Response (dated Apr. 1, 2011) in related European Patent Application No. EP 2007 0843228.3.

\* cited by examiner

$T_R$ [0.4 | 1.2 | 1.5 | 0.3] × W $\begin{bmatrix} 1 & 0 & 0 & 0 \\ 0 & 1.5 & 0 & 0 \\ 0 & 0 & 1.5 & 0 \\ 0 & 0 & 0 & 1 \end{bmatrix}$ = $T_W$ [0.4 | 1.8 | 2.25 | 0.3]

$S_R$ [0.5 | 1.1 | 1.4 | 0.4] × W $\begin{bmatrix} 1 & 0 & 0 & 0 \\ 0 & 1.5 & 0 & 0 \\ 0 & 0 & 1.5 & 0 \\ 0 & 0 & 0 & 1 \end{bmatrix}$ = $S_W$ [0.5 | 1.65 | 2.1 | 0.4]

SIGNAL ANALYSIS IN IMPLANTABLE CARDIAC TREATMENT DEVICES

RELATED APPLICATIONS

This application is a divisional of U.S. application Ser. No. 11/527,184, filed Sep. 26, 2006 published as US 2008-0077030 A1, and titled SIGNAL ANALYSIS IN IMPLANTABLE CARDIAC TREATMENT DEVICES, now U.S. Pat. No. 8,014,851, the entire disclosure of which is herein incorporated by reference.

FIELD

The present invention is related to the field of implantable medical devices. More particularly, the present invention relates to methods of analyzing cardiac signals.

BACKGROUND

Pacemakers and implantable cardioverter/defibrillators (ICDs) have become useful treatment devices for those with cardiac dysfunction. These devices provide electrical stimulus that helps a patient's heart function properly. One aspect of such devices is the desire to accurately identify whether and when a patient is experiencing a malignant cardiac condition. However, the heart may experience not only normal sinus rhythms but also various forms of arrhythmias, such as atrial fibrillation, atrial tachycardias, ventricular fibrillation, and ventricular tachycardias. Not all of these arrhythmias are malignant. Because the application of cardioversion or defibrillation stimulus can be discomforting to a patient, unnecessary application of stimulus should be avoided. Further, erroneous application of stimulus can cause a patient's heart to enter a malignant cardiac condition such as fibrillation. Methods and devices that provide additional approaches to discriminating between malignant and non-malignant cardiac conditions are therefore desired.

SUMMARY

The present invention, in an illustrative embodiment, includes a method of cardiac signal analysis, the method comprising capturing a cardiac signal by the use of first and second electrodes disposed within a patient, detecting a cardiac event, conditioning a portion of the cardiac signal associated with the cardiac event, and analyzing the portion of the cardiac signal to determine whether the patient is likely experiencing a malignant cardiac condition. The step of conditioning a portion of the cardiac signal associated with the cardiac event may include sampling the cardiac signal to generate a number of samples and comparing a selected sample to a sample threshold and, if the sample magnitude does not exceed the sample threshold, replacing the sample with a different value.

In some embodiments, the samples are at least temporarily stored in a form having a least amplitude and a greatest amplitude, wherein, if the sample magnitude does not exceed the sample threshold, the method includes replacing the selected sample with a value corresponding to the least amplitude. In another embodiment, the samples are at least temporarily stored in a signed format, wherein, if the sample magnitude does not exceed the sample threshold, the method includes replacing the selected sample with a value corresponding to a zero in the signed format. If the sample magnitude does not exceed the sample threshold, the method may include replacing the selected sample with a value corresponding to the sample threshold.

In some embodiments, the step of analyzing the portion of the cardiac signal includes comparing the portion of the cardiac signal to a stored template, wherein the stored template includes a number of template samples and, if one or more of the template samples do not exceed the threshold, those template samples are marked, and the selected sample of the portion of the cardiac signal is selected such that it corresponds to a marked sample of the template when the portion of the cardiac signal is compared to the stored template. The method may further include weighting the sample vector to give some signal samples greater analytical weight than others. In some embodiments, the step of analyzing the portion of the cardiac signal may include a step of comparing the portion of the cardiac signal to a stored template and the comparing step includes weighting certain samples of the portion of the cardiac signal more than other samples.

The present invention, in another illustrative embodiment, includes a method of cardiac signal analysis, the method comprising capturing a cardiac signal by the use of first and second electrodes disposed within a patient, detecting a cardiac event, sampling the cardiac signal, treating the sampled signal as a sample vector, and multiplying the sample vector by a weighting vector to yield a weighted sample vector, and analyzing the weighted sample vector to determine whether the patient is likely experiencing a malignant cardiac condition. In some embodiments, the weighting vector may have at least some components that are greater than at least some other components within the weighting vector. In yet another method, the sample vector includes a component identified as a fiducial point for the sample vector, and the weighting vector has a peak component corresponding to the fiducial point within the sampled vector, the peak component having a greater amplitude than other components of the weighting vector.

Another illustrative embodiment includes a method of determining whether a patient is undergoing a malignant cardiac condition comprising capturing a cardiac signal having a cardiac event from a patient using implanted electrodes, sampling the cardiac signal such that it is comprised of a number of signal samples, and comparing the cardiac signal to a stored template to yield a score indicative of correlation between the cardiac signal and the stored template, wherein at least some of the signal samples are provided with greater weight during the comparison and others of the signal samples are provided with a lesser weight during the comparison. In one embodiment, the cardiac signal includes a fiducial point, and greater weight is given to samples nearer the fiducial point than other samples. In another embodiment, the cardiac signal includes one or more slopes, wherein lesser weight is given to samples taken along a sloped portion of the cardiac signal.

Yet another illustrative embodiment includes a method of cardiac signal analysis, the method comprising capturing a cardiac signal by the use of first and second electrodes disposed within a patient, detecting a cardiac event, conditioning a portion of the cardiac signal associated with the cardiac event, and analyzing the portion of the cardiac signal to determine whether the patient is likely experiencing a malignant cardiac condition. The step of detecting a cardiac event may include observing whether a captured cardiac signal exceeds a threshold value in the following manner: after a previous cardiac event, selecting a refractory period; identifying peak signal amplitudes of one or more previous cardiac events and selecting first and second thresholds related to the peak signal amplitudes, the first threshold having a greater value than the second threshold; and generating the threshold value with a continuously decreasing value over a time following the refractory period and before sensing of a next cardiac event, the threshold value having a first value equal to the first threshold and, at a later point in time, having a value approaching the second threshold.

In some embodiments, the first threshold is at least 50 percent of an average of a number of previous peak signal amplitudes. In yet additional embodiments, the second threshold is less than 10 percent of an average of a number of previous peak signal amplitudes. These values may be adaptive, for example, one percentage or the other may vary over time if false detections are identified. The step of analyzing may include comparing the cardiac signal to a stored template and providing greater weight to comparisons of first corresponding portions of the cardiac signal and the template, and lesser weight to comparisons of second corresponding portions of the cardiac signal and the template. The first corresponding portions may correspond to greatest amplitude portions of the cardiac signal. The second corresponding portions may correspond to greatest slope regions of the cardiac signal. The step of analyzing may include observing whether certain portions of the cardiac signal have a magnitude that exceeds a sample threshold and, if not, replacing those portions of the cardiac signal with a preselected value.

DETAILED DESCRIPTION

The following detailed description should be read with reference to the drawings. The drawings, which are not necessarily to scale, depict illustrative embodiments and are not intended to limit the scope of the invention.

To date, implantable cardiac treatment systems have been either epicardial systems or transvenous systems. For example, transvenous systems can be implanted generally as shown in FIG. 1B. However, as further explained herein, the present invention is also adapted to function with a subcutaneous implantable cardiac treatment system as shown in FIG. 1A.

Figure 1A:
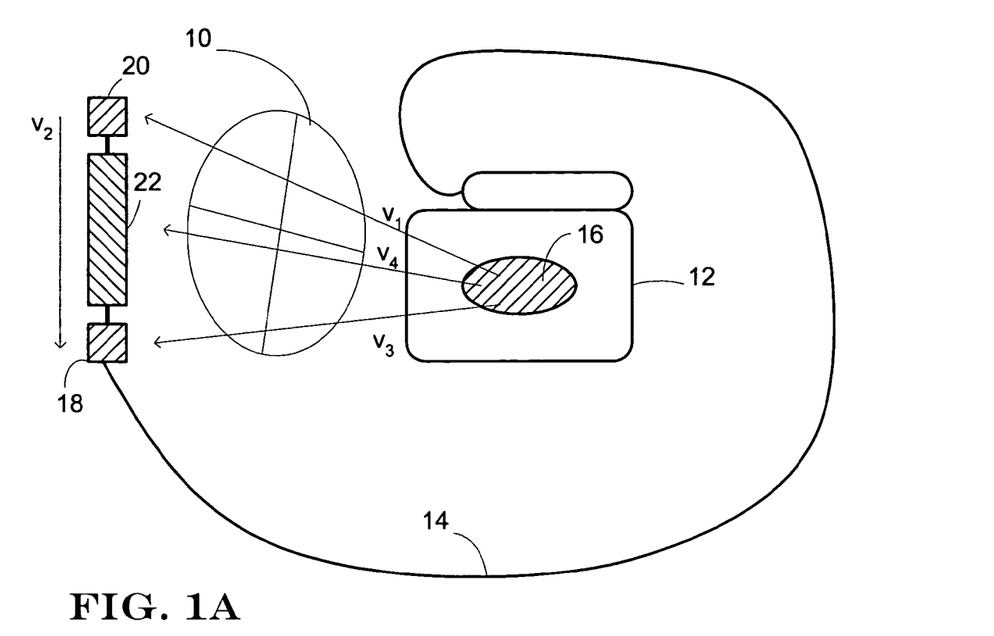
FIGS. 1A and 1B illustrate two example configurations for implantable cardiac treatment devices.
Figure 1B:
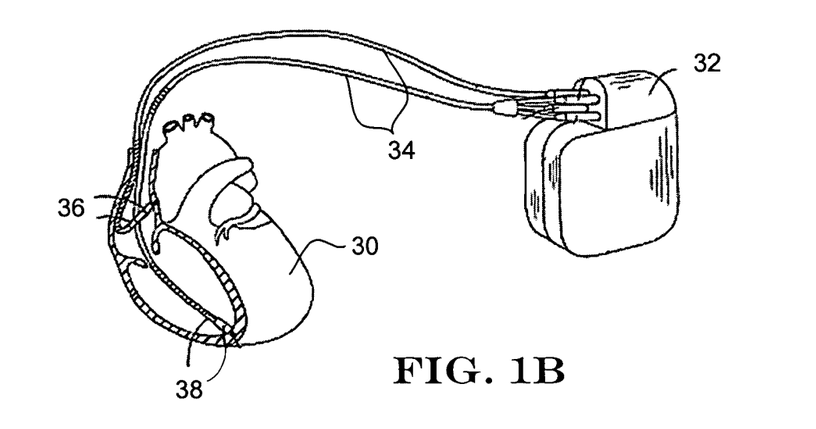

FIG. 1A illustrates a subcutaneously placed implantable cardiac treatment system, in particular, an ICD system. In this illustrative embodiment, the heart 10 is monitored using a canister 12 coupled to a lead system 14. The canister 12 may include an electrode 16 thereon, while the lead system 14 connects to sensing electrodes 18, 20, and a coil electrode 22 that may serve as a shock or stimulus delivery electrode as well as a sensing electrode. The various electrodes define a number of sensing vectors V1, V2, V3, V4. It can be seen that each vector provides a different vector "view" of the heart's 10 electrical activity. The system may be implanted subcutaneously as illustrated, for example, in U.S. Pat. Nos. 6,647,292 and 6,721,597, the disclosures of which are both incorporated herein by reference. By subcutaneous placement, it is meant that electrode placement does not require insertion of an electrode into a heart chamber, in or on the heart muscle, or the patient's vasculature.

FIG. 1B illustrates a transvenous ICD system. The heart 30 is monitored and treated by a system including a canister 32 coupled to a lead system 34 including atrial electrodes 36 and ventricular electrodes 38. A number of configurations for the electrodes may be used, including placement within the heart, adherence to the heart, or disposition within the patient's vasculature.

Figure 2:
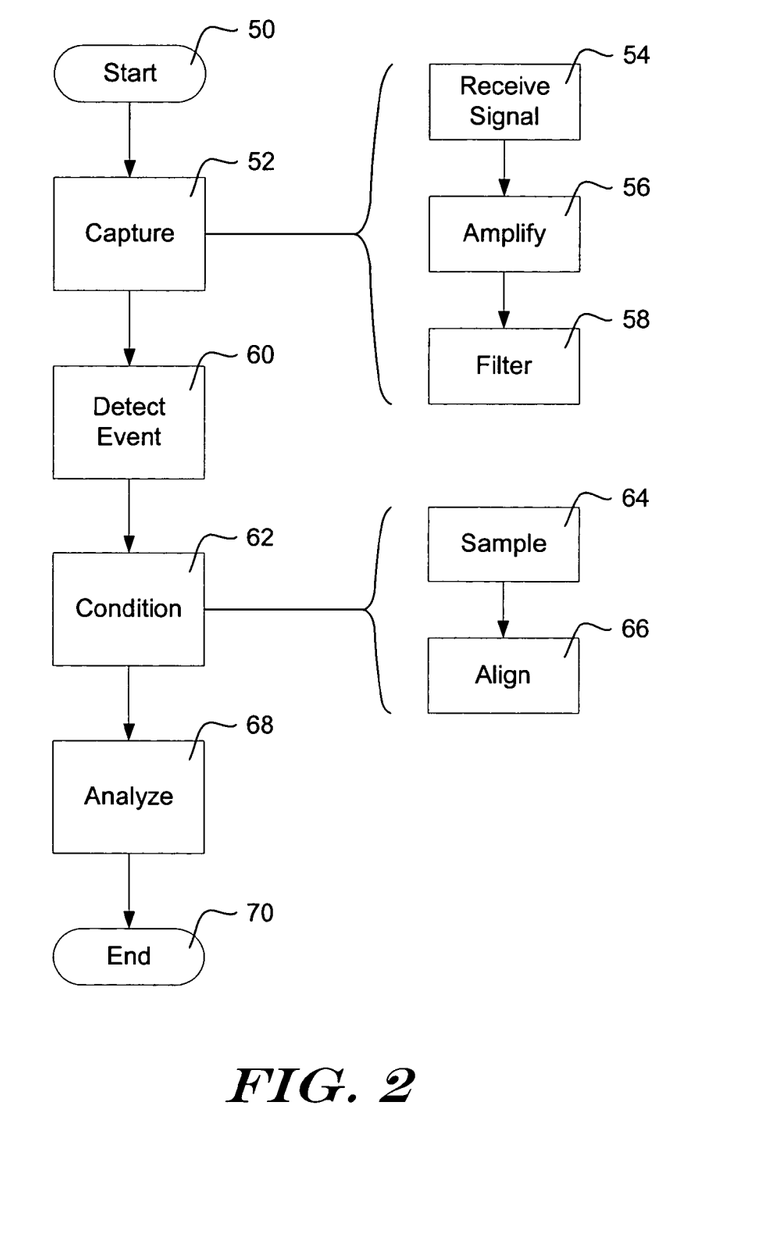
FIG. 2 shows in block form an example of cardiac signal analysis.

FIG. 2 shows in block form an example of cardiac signal analysis. From start block 50, the cardiac signal is captured, as shown at 52. The capture step 52 may include several subparts as shown to the right on FIG. 2. A first step may be receiving a signal 54, which may be performed, for example, using electrodes disposed within a patient as shown in FIGS. 1A-1B, and/or by the use of additional or other suitable implanted electrode configurations. The signal is then amplified to a level more suitable for electrical manipulation, as shown at 56, and filtered to remove known noise (50/60 Hz noise, for example) as well as extraneous data (signals with frequencies above 100 Hz or so, for example), as shown at 58.

After signal capture 52, the next step is to detect whether a cardiac event has occurred, as shown at 60. If so, then the cardiac signal is further conditioned, as shown at 62, which may include sampling 64 to turn the analog signal into a digital signal. Alternatively, event detection may take place using a digitized signal. In some embodiments, the signal is also aligned 66 and placed into a windowed format for further analysis. Some illustrative examples of such alignment are shown in U.S. patent application Ser. No. 10/858,598, filed Jun. 1, 2004, now U.S. Pat. No. 7,248,921 and titled METHOD AND DEVICES FOR PERFORMING CARDIAC WAVEFORM APPRAISAL, the disclosure of which is incorporated herein by reference.

Once the cardiac event has been conditioned 62, the signal is analyzed, as shown at 68. Analysis may take a number of forms. Rate measurement is one form of analysis; in some prior devices rate measurement was a sole method of analysis. The present invention may include the use of morphology analysis as set forth in U.S. patent application Ser. No. 10/856,084, filed May 27, 2004, now U.S. Pat. No. 7,330,757 and titled METHOD FOR DISCRIMINATING BETWEEN VENTRICULAR AND SUPRAVENTRICULAR ARRHYTHMIAS, the disclosure of which is incorporated herein by reference.

The present invention, in several embodiments, provides additional details to parts of the method shown in FIG. 2. In one example embodiment, the step of detecting an event 60 may include comparing a received signal to a time-changing event threshold. The method for changing the event threshold may be performed in a manner further set forth below. In another embodiment, the step of conditioning the signal 62 may include an additional step of suppressing certain portions of the signal area of an amplitude that does not exceed a suppression threshold. In another embodiment, the steps of conditioning 62 and/or analyzing 68 may further include weighting the cardiac signal for or during analysis. For example, the cardiac signal may comprise a number of samples, with some samples given greater weight either during conditioning 62 or analysis 68.

Figure 3:
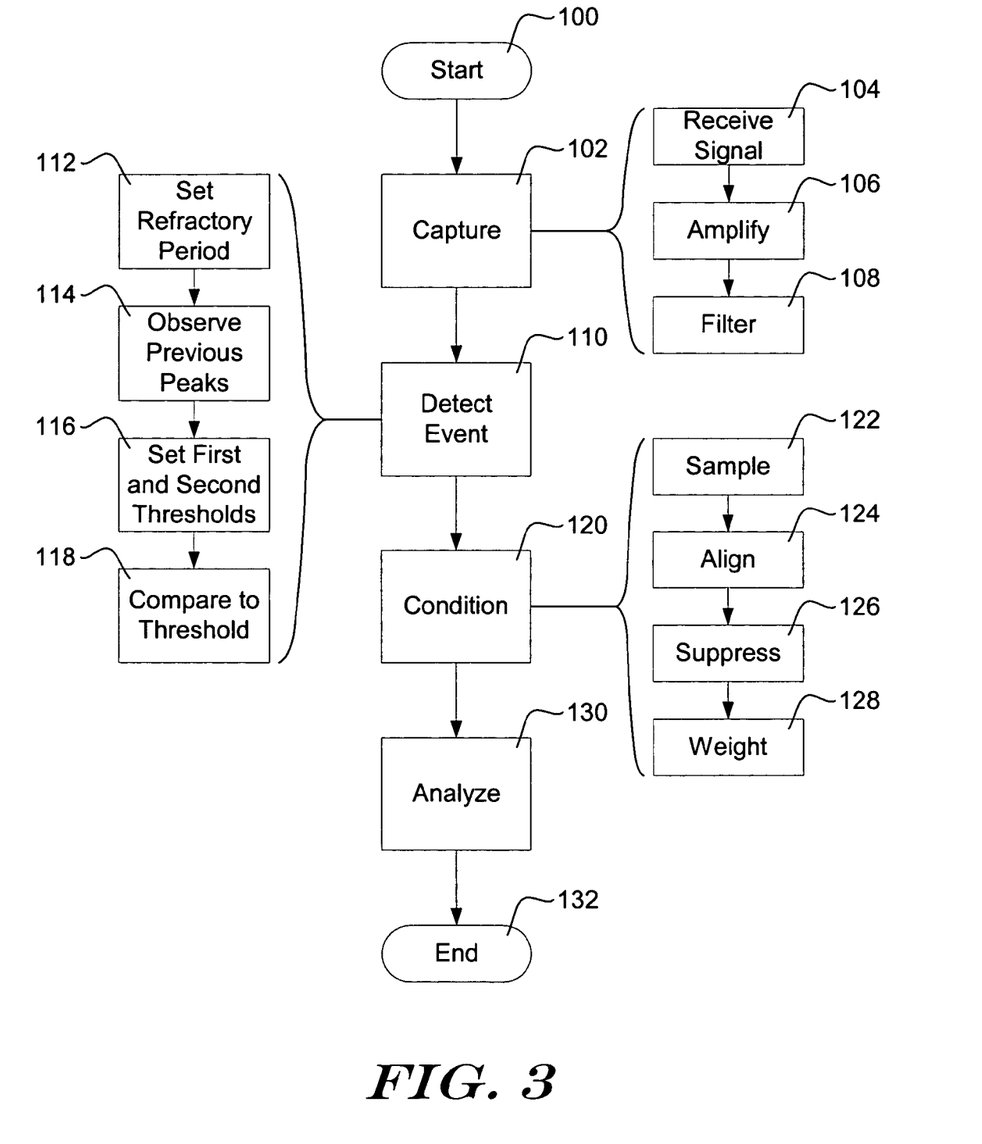
FIG. 3 shows in block form an illustrative embodiment of a method for cardiac signal analysis.

FIG. 3 shows in block form an illustrative embodiment of a method for cardiac signal analysis. The illustrative method of FIG. 3 includes each of the above noted improvements, although it should be understood that the methods, subroutines or sub-methods disclosed herein may be used in combination or separately unless otherwise specified. Further, certain steps may be interchanged or performed in a different order, as desired.

The example method of cardiac signal analysis begins at start block 100 and includes capturing signals, as shown at 102. The capture step 102 may include receiving a signal from implanted electrodes as shown at 104, amplifying the signal as shown at 106, and filtering the signal as shown at 108. The amplify and filter steps 106, 108 may be interchanged, and additional filtering stages may be provided.

Once a signal has been captured at 102, the method continues with detecting an event, as shown at 110. The step of detecting an event may include a subroutine as shown on the left of the Figure. The subroutine may include, after sensing a previous event, setting a refractory period, as shown at 112. During the refractory period, an event will not be detected. Also included in the event detection subroutine is the step of observing previous peak amplitudes, as shown at 114. First and second thresholds are set using the previous peak amplitudes, as shown at 116. In an illustrative example, the first threshold is a threshold level above which detection occurs shortly after the end of the refractory period, and the second threshold is a threshold level above which detection occurs later on in time. A linear or exponential curve may be used to define the threshold. In some embodiments, the first threshold is a first, relatively higher percentage of an average of at least two previous peaks, and the second threshold is a second, relatively lower percentage of an average of at least two previous peaks. A constant may be added to either threshold. Further explanation of an illustrative threshold is provided below by reference to FIG. 4.

With the thresholds set, the event detection subroutine then includes comparing a received signal to the threshold, as shown at 118. When the received signal exceeds the threshold, an event may be declared. If desired, an event or waveform appraisal method may be used in addition to that shown, for example, methods of validation such as those set forth in U.S. patent application Ser. No. 10/858,598, filed Jun. 1, 2004, now U.S. Pat. No. 7,248,921 and titled METHOD AND DEVICES FOR PERFORMING CARDIAC WAVEFORM APPRAISAL, the disclosure of which is incorporated herein by reference.

After an event has been detected at 110, the method continues by conditioning a received signal corresponding to the detected event, as shown at 120. The conditioning step 120 may include a subroutine as shown to the left in the Figure. The cardiac signal may be sampled, as shown at 122, to digitize the analog signal. Next the sampled signal may be aligned for purposes of comparing the signal to a saved cardiac template, as shown at 124.

Within the conditioning step 120, the sampled cardiac signal may undergo a suppression step as shown at 126. For example, a threshold below which samples are "zeroed" out may be defined. If a correlation analysis comparison with a template is used, then the suppression step may reduce the effects of noise on analysis. Next, the sampled, aligned, and suppressed cardiac signal may be subjected to a weighting step, as shown at 128. During the weighting step 128, certain samples are given greater analytical weight than other samples.

After the conditioning step 120, the method next includes analyzing the signal, as shown at 130. Analysis may include, for example, comparison to a stored or dynamic template. Analysis may also include other morphology or rate considerations, such as measurement of R-R intervals or QRS width. The method of processing and analyzing the cardiac signal then ends, as shown at 132. From the method of FIG. 3, a decision may be made as to whether or not the patient appears to be experiencing a malignant cardiac condition, as well as whether treatment is indicated.

Figure 4:
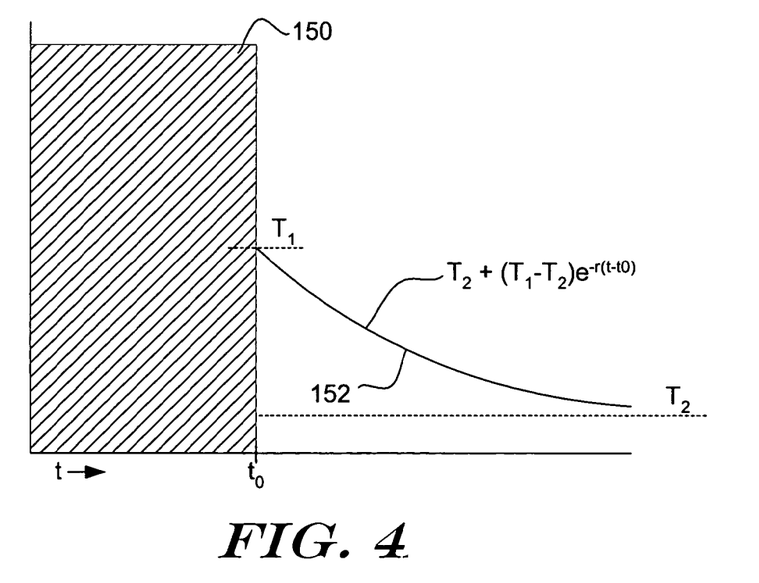
FIG. 4 illustrates, graphically, methods of R-wave detection in accordance with an illustrative method.

FIG. 4 illustrates, graphically, methods of R-wave detection in accordance with an illustrative sub-method. The method is illustrated using a continuous function, although in practice the signal(s) involved often may be discrete, sampled signals. During the illustrative R-wave detection method, a refractory period is represented by block 150, during which the R-wave detector is either disabled or during which detections by the R-wave detector are ignored. After a time $t_0$, a threshold 152 is defined and used. The threshold 152 begins at a first threshold $T_1$ and asymptotically approaches a second threshold $T_2$, following a logarithmic formula as shown in the Figure:

$$\text{Threshold\_152} = T_2 + (T_1 - T_2) * e^{-r(t-t_0)}$$

The first and second thresholds $T_1$ and $T_2$ may be selected as a defined percentage of a previous peak or average of previous peak detected signals.

In one embodiment, the first threshold $T_1$ is set at 35-75% of the average of two previous peaks and the second threshold $T_2$ is set at 2-20% of the average of two previous peaks. In another embodiment, the first threshold $T_1$ is set at 50-60% of the average of two previous peaks and the second threshold $T_2$ is set at 2.5-7.5% of the average of the two previous peaks. In yet another embodiment, the first threshold $T_1$ is set at about 55% of the average of the two previous peaks, while the second threshold $T_2$ is set at about 5% of the average of the two previous peaks. The first and second thresholds may vary, for example, depending upon a patient's heart activity or cardiac signal characteristics, electrode location, or other suitable factors. For example, one or the other of the first and second threshold percentages may be adaptive and may vary depending upon the detected event rate of the patient, the signal-to-noise ratio, or another factor.

By placing the sensing thresholds in the range of a percentage of a recent peak, the R-wave detection method becomes adaptive to changes in patient cardiac electrical activity.

Figure 5A:
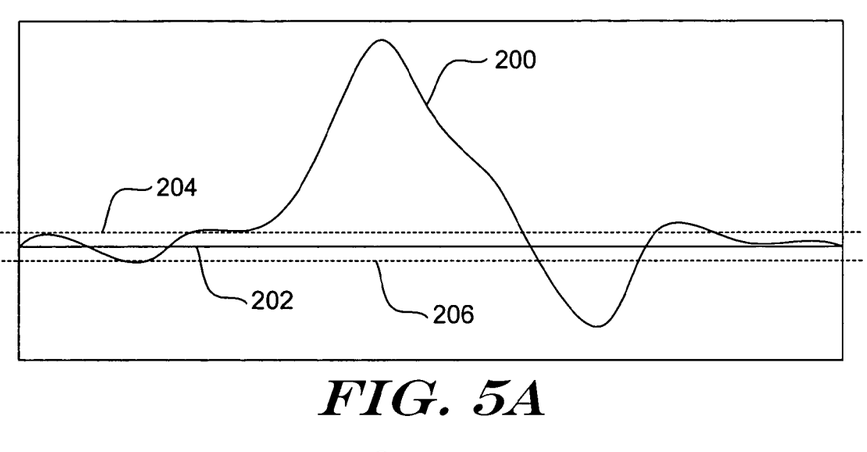
FIGS. 5A-5C show, graphically, an illustrative example method of conditioning a captured cardiac signal.
Figure 5B:
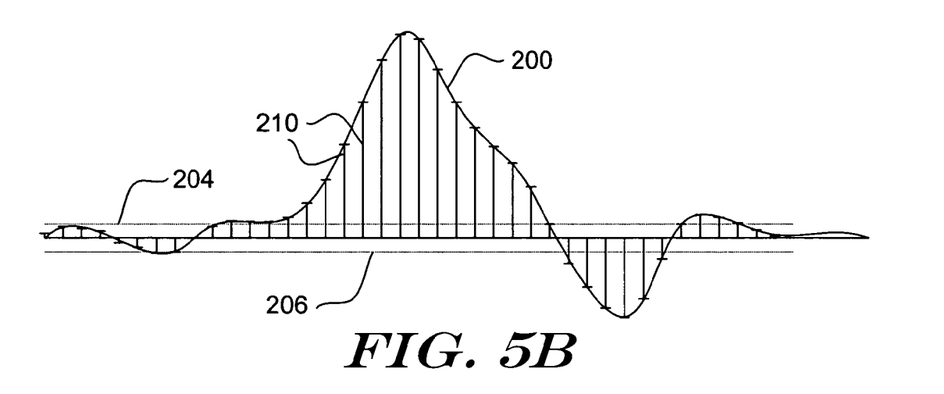
Figure 5C:
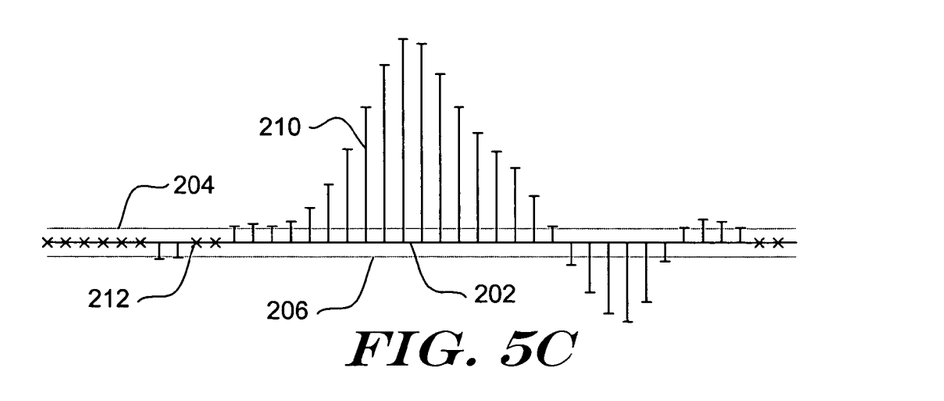

FIGS. 5A-5C show, graphically, an illustrative example method of conditioning a captured cardiac signal. Referring to FIG. 5A, a received signal 200 is shown corresponding to a relatively normal cardiac event having QRS features. The signal 200 is shown in analog form around a baseline 202. Sample thresholds 204, 206 are shown around the baseline 202. FIG. 5B illustrates sampling of the signal 200 of FIG. 5A. It can be seen that samples 210 provide periodic representation of the signal 200, enabling digital manipulation of the signal. Some samples do not exceed the thresholds 204, 206. Referring to FIG. 5C, only the sampled representation 210 is shown. Some of the samples have been replaced by "X" symbols, such as samples 212. These samples are samples which did not exceed the thresholds 204, 206 and have therefore been replaced, using the illustrative method, with the baseline value.

The thresholds 204, 206 are shown as symmetric thresholds about a baseline 202. In other embodiments, the thresholds 204, 206 may be asymmetric instead. In some embodiments, an absolute value may be taken, rather than signed values, as shown, such that only one threshold is defined. The thresholds 204, 206 may be set to a value that is sufficiently low that it may be surmised that, rather than cardiac signal, a sample falling within the thresholds 204, 206 is dominated by noise. In some embodiments the thresholds are set to constant levels. Alternatively, thresholds 204, 206 can be set to a percentage in the range of 1% to 5% of peak signal amplitude or adaptive over time using, for example, knowledge of the received cardiac signal. In the digital domain, another threshold level may be to make use of the digital characteristics of the signals once sampled. For example, in a system having 256-step resolution (an 8-bit system) operating on absolute values, samples with values between 0000 0000 and 0000 1000 may be set to 0000 0000. In another embodiment, signals falling below threshold 204 and above baseline 202 may be set to the value of threshold 204, and signals falling above threshold 206 and below baseline 202 are set to the value of threshold 206.

Figure 6A:
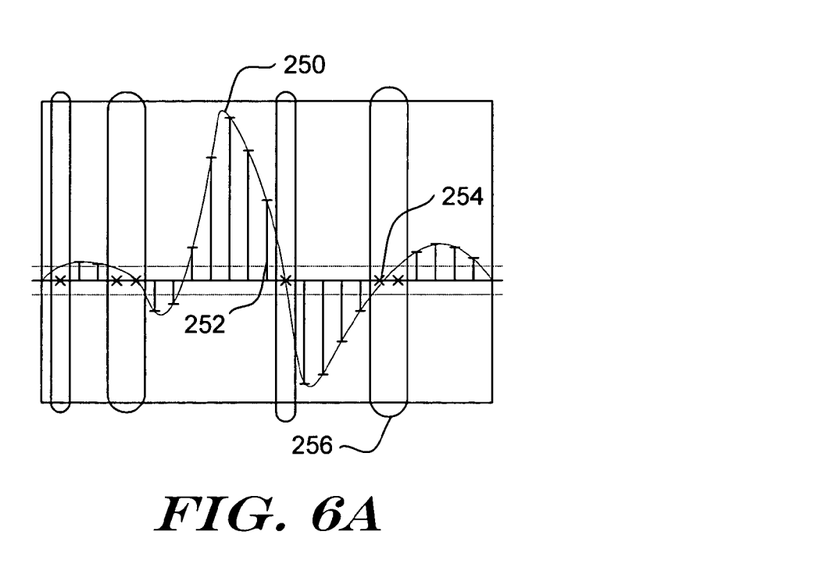
FIGS. 6A-6B illustrate another thresholding operation.

FIGS. 6A-6B illustrate another thresholding operation. FIG. 6A illustrates thresholding performed on a template. The template signal 250 is illustratively shown, with samples 252 representing the actual template. The template may be used for comparing to a received signal for the purpose of determining whether the received signal likely corresponds to a malignant cardiac event. Some samples 254 are shown "zeroed out" to the baseline value in a method according to that discussed by reference to FIGS. 5A-5C. These samples are marked, as indicated by thresholding block 256.

Figure 6B:
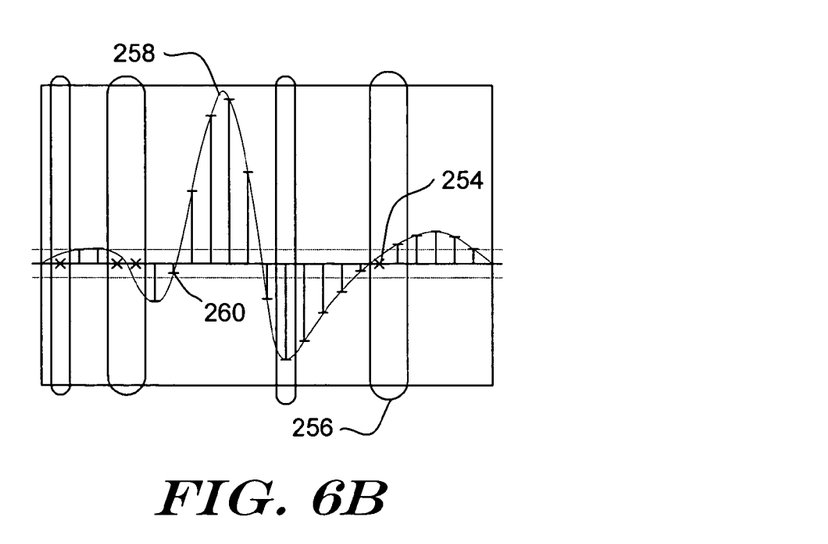

Referring to FIG. 6B, treatment of a received signal 258 is shown. It can be seen that a sample 260 falls between the sample thresholds and the baseline. However, sample 260 does not fall within a thresholding block 256, and so the threshold comparison is not performed for this sample. Instead, for samples within the thresholding block 256, the threshold comparison is performed, and sample 254 is zeroed out. The method of FIGS. 6A-6B thus calls for marking which samples have been subjected to thresholding in the template of FIG. 6A for the purpose of conditioning the received sample 258 in FIG. 6B.

Figure 7:
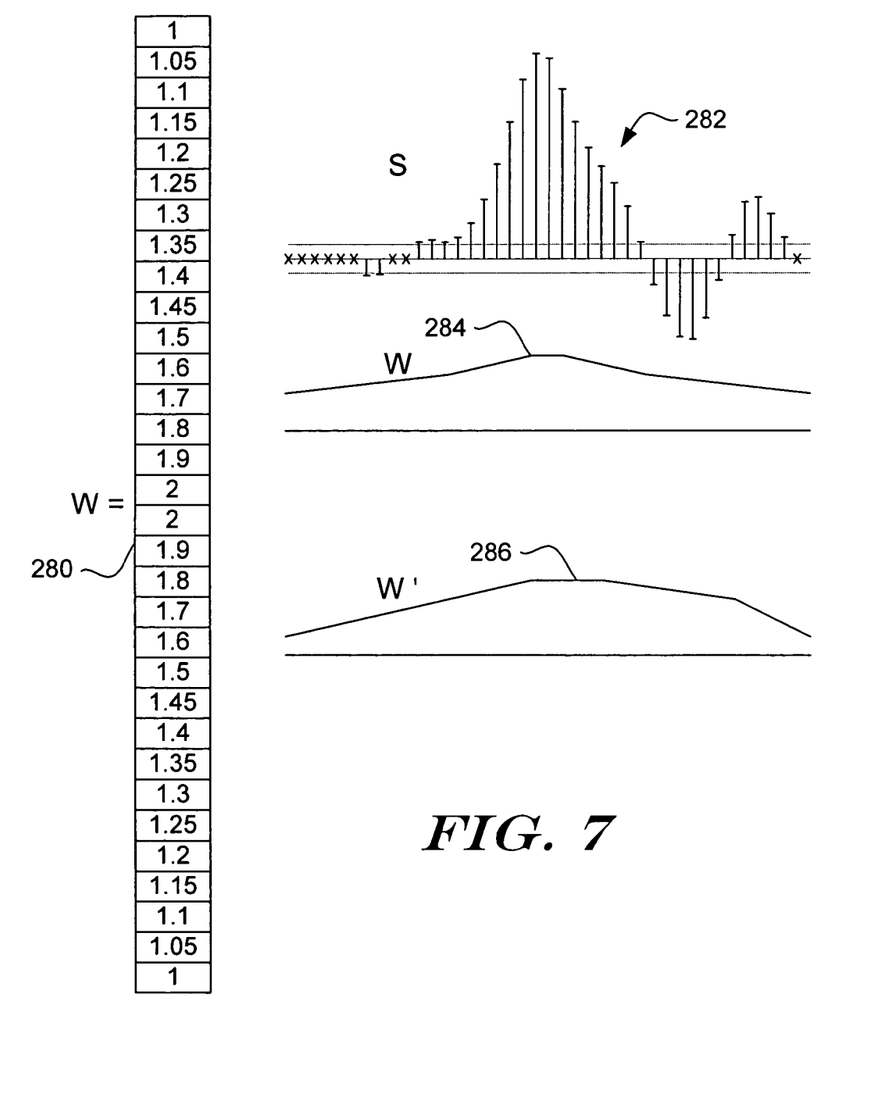
FIG. 7 shows in graphical and numeric format some example embodiments for weighting vectors.

FIG. 7 shows in graphical and numeric format some example embodiments for weighting vectors. A weight vector W 280 is shown numerically as including a number of values. In the illustrative example, signal S includes a number of samples 282, with the size of the weight vector 280 being chosen to correspond to the number of samples 282. The graphical form of W is shown at 284. It can be seen that the greatest weight is given to samples in the center of the signal S. One reason to place greater weight in this region of the signal S is that the center portion of the received signal may likely contain more dramatic morphology data assuming that some semblance of a QRS-type cardiac event can be detected. Further, this region may be emphasized as it is the region where greatest deviation from the baseline, and the signal most likely to contain the least relative amount of noise, can be found.

By the use of a vector cross product, the signal S can be modified using the weight vector 280. With the method of FIG. 7, additional analysis may include correlation waveform analysis. An example formula for such analysis is the following:

$$\text{CWA\_Score } (\%) = 1 - \frac{\sum_i |a*(t_i) - s_i|}{\sum_i |a*(t_i)|} *100$$

where: $t_i$ is the value of the $i^{th}$ template sample, $s_i$ is the value of the $i^{th}$ signal sample, a is a scaling factor calculated as a ratio of the signal peak to the template peak, and i is the number of samples in the template and signal. The use of a weighting factor as part of signal conditioning is based on application of the formula:

$$s_i = w_i \times r_i$$

where $w_i$ is the value of the $i^{th}$ weighting factor and $r_i$ is the value of the $i^{th}$ unweighted or raw data sample. Likewise for the template:

$$t_i = w_i \times tr_i$$

where $tr_i$ is the raw template value.

Figure 8:
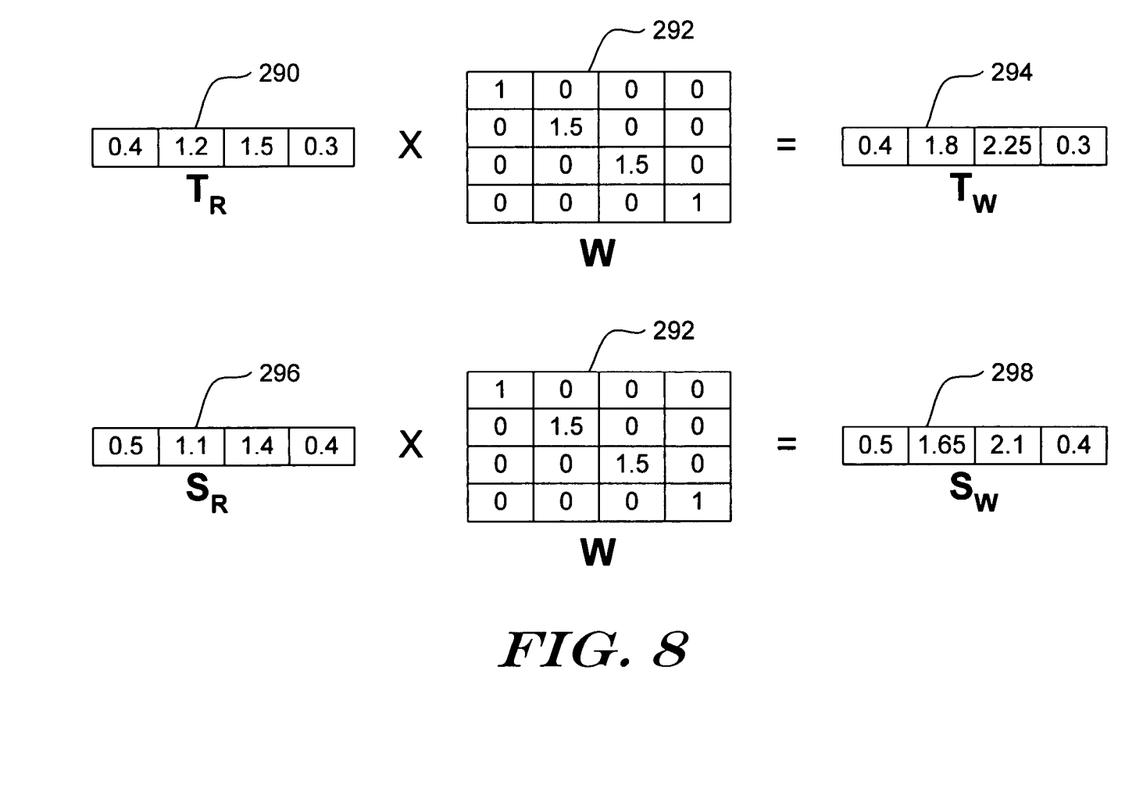
FIG. 8 shows mathematical treatment of a sample using a weighting matrix.

FIG. 8 shows mathematical treatment of a sample using a weighting matrix. The mathematical operation of FIG. 8 is greatly simplified for illustrative purposes. In essence, the template vector 290 is crossed with a diagonal weighting matrix 292 having diagonal values corresponding to the weighting vector to yield a weighted template vector 294. Likewise, the cross product of the sample vector 296 with the diagonal weighting matrix 292 yields a weighted sample vector 298. The weighted template vector 294 and weighted sample vector 298 may then be used in further analysis.

While FIGS. 7-8 assume that signal conditioning is used to provide the weighting function, the signal may also be provided with added weight during analysis. Returning to the above formula for CWA, a weighting vector may be taken into account in the formula:

$$\text{CWA\_Score } (\%) = 1 - \frac{\sum_i |w_i * [a*(t_i) - s_i]|}{\sum_i |w_i * a*(t_i)|} *100$$

Again, $w_i$ is the value of the $i^{th}$ weighting factor. With the above formula, the weighting vector can be used to modify the CWA analysis.

Figure 9:
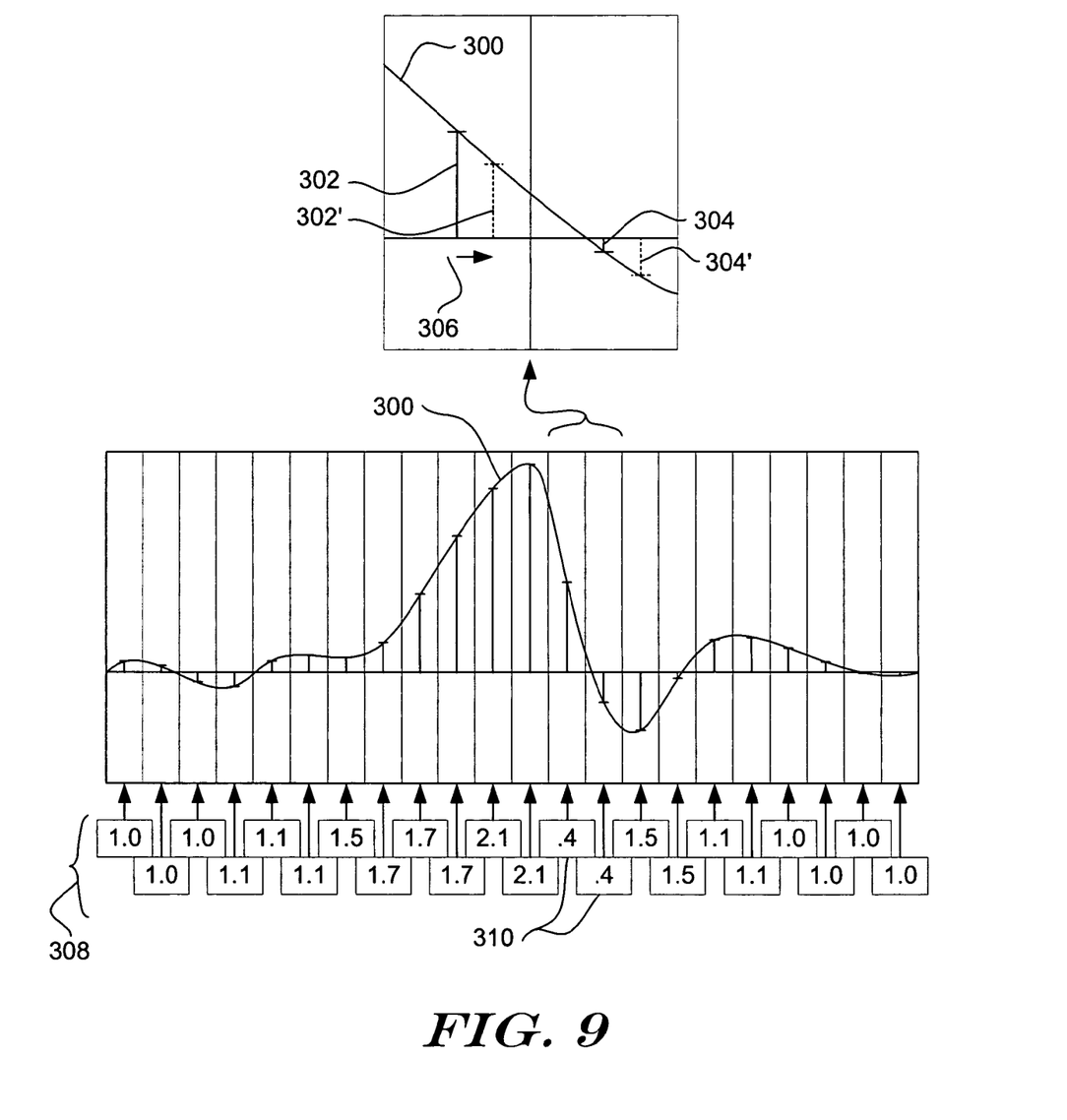
FIG. 9 illustrates another approach to a weighting vector/operation.

FIG. 9 illustrates another approach to a weighting vector/operation. A signal 300 is shown sampled in a number of sample blocks. After a peak, signal 300 drops off with a large downward slope. A portion of the signal 300 is shown blown up in the upper portion of FIG. 9. There it can be seen that samples 302 and 304 are taken of signal 300. However, a slight change of timing, indicated by skew 306, results in samples 302', 304', rather than samples 302, 304. This means that, due to the steep slope of signal 300, a small skew of the sampling results in a significant change of the samples, with sample 302' having a smaller magnitude and lower value, while sample 304' has a greater magnitude and more negative value. The skewing of the samples causes one sample to have a lesser amplitude and lesser magnitude, while the other has a more negative amplitude and greater magnitude. The weighting vector, however, which is shown at 308, may account for the likelihood of such effects along the steepest slope region. Specifically, it can be seen that the least weight is given by the portion 310 of the weighting vector 308 corresponding to the steep slope. Meanwhile, at more gradually sloped locations, higher weight is given. The example shown in FIG. 9 is merely another illustrative manner in which a received signal may be weighted.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of cardiac signal analysis in an implantable cardiac system comprising a plurality of implantable electrodes for sensing signals from implanted locations coupled to circuitry for analysis of sensed signals, the method comprising:
   capturing a cardiac signal by the use of the plurality of electrodes;
   detecting a cardiac event;
   conditioning a portion of the cardiac signal associated with the cardiac event; and
   analyzing at least some parts of the conditioned portion of the cardiac signal to determine whether the patient is likely experiencing a malignant cardiac condition;
   wherein the step of conditioning a portion of the cardiac signal associated with the cardiac event includes sampling the cardiac signal to generate a number of samples and comparing a selected sample to a sample threshold and, if the sample magnitude does not exceed the sample threshold, replacing the sample with a different value.

2. The method of claim 1, wherein the samples are at least temporarily stored in a form having a least amplitude and a greatest amplitude, wherein, if the sample magnitude does not exceed the sample threshold, the method includes replacing the selected sample with a value corresponding to the least amplitude.

3. The method of claim 1, wherein the samples are at least temporarily stored in a signed format, wherein, if the sample magnitude does not exceed the sample threshold, the method includes replacing the selected sample with a value corresponding to a zero in the signed format.

4. The method of claim 1, wherein, if the sample magnitude does not exceed the sample threshold, the method includes replacing the selected sample with a value corresponding to the sample threshold.

5. The method of claim 1, wherein the step of analyzing the portion of the cardiac signal includes comparing the conditioned portion of the cardiac signal to a stored template, wherein the stored template includes a number of template samples and, if one or more of the template samples do not exceed the threshold, those template samples are marked, and the selected sample of the portion of the cardiac signal is selected such that it corresponds to a marked sample of the template when the portion of the cardiac signal is compared to the stored template.

6. The method of claim 5, wherein the step of comparing the conditioned portion of the cardiac signal to the stored template yields a series of comparison values, and the step of analyzing the portion of the cardiac signal further includes performing a vector multiplication of the series of comparison values with a series of weighting values to yield a set of weighted comparison values and then summing the series of weighted comparison values to generate a value indicative of the degree of correlation of the cardiac signal to the stored template.

7. The method of claim 6, wherein the series of comparison values is performed by calculating a difference between a sample of the conditioned portion of the cardiac signal and a corresponding sample of the stored template.

8. The method of claim 6, wherein the step of conditioning a portion of the cardiac signal includes normalizing a series of amplitudes of the cardiac signal.

9. The method of claim 1, further comprising weighting certain sample to give some signal samples greater analytical weight than others.

10. The method of claim 1, wherein the step of analyzing the portion of the cardiac signal includes a step of comparing the portion of the cardiac signal to a stored template and the comparing step includes weighting certain samples of the portion of the cardiac signal more than other samples.

11. An implantable cardiac stimulus device (ICSD) comprising a plurality of implantable electrodes for sensing signals from implanted locations and operational circuitry coupled to the electrodes and configured to analyze sensed signals and, as determined by the analysis of sensed signals, deliver therapy to a patient, wherein the operational circuitry is configured to perform the following steps to analyze sensed signals:
   receive a cardiac signal captured by the use of the plurality of electrodes;
   detecting a cardiac event in the cardiac signal;
   conditioning a portion of the cardiac signal associated with the cardiac event; and
   analyzing at least some parts of the conditioned portion of the cardiac signal to determine whether the patient is likely experiencing a malignant cardiac condition by comparison of the conditioned portion of the cardiac signal to a stored template;
   wherein the step of conditioning a portion of the cardiac signal associated with the cardiac event includes sampling the cardiac signal to generate a number of samples and comparing a selected sample to a sample threshold and, if the sample magnitude does not exceed the sample threshold, replacing the sample with a different value.

12. The ICSD of claim 11, wherein the operational circuitry is configured such that the samples are at least temporarily stored in a form having a least amplitude and a greatest amplitude, wherein, if the sample magnitude does not exceed the sample threshold, the method includes replacing the selected sample with a value corresponding to the least amplitude.

13. The ICSD of claim 11, wherein the operational circuitry is configured such that the stored template includes a number of template samples and, if one or more of the template samples do not exceed the threshold, those template samples are marked, and the selected sample of the portion of the cardiac signal is selected such that it corresponds to a marked sample of the template when the portion of the cardiac signal is compared to the stored template.

14. The ICSD of claim 13, wherein the operational circuitry is configured such that the step of comparing the conditioned portion of the cardiac signal to the stored template yields a series of comparison values, and the step of analyzing the portion of the cardiac signal further includes performing a vector multiplication of the series of comparison values with a series of weighting values to yield a set of weighted comparison values and then summing the series of weighted comparison values to generate a value indicative of the degree of correlation of the cardiac signal to the stored template.

15. The ICSD of claim 11, wherein the operational circuitry is further configured to apply a weighting factor vector to the samples to give some signal samples greater analytical weight than others.

16. An implantable cardiac stimulus device (ICSD) comprising a plurality of implantable electrodes for sensing signals from implanted locations, and means for analyzing sensed signals which is configured to perform the following to analyze sensed signals:
   receiving a cardiac signal captured by the use of the plurality of electrodes;
   detecting a cardiac event in the cardiac signal;
   conditioning a portion of the cardiac signal associated with the cardiac event; and analyzing at least some parts of the conditioned portion of the cardiac signal to determine whether the patient is likely experiencing a malignant cardiac condition by comparison of the conditioned portion of the cardiac signal to a stored template;

wherein the step of conditioning a portion of the cardiac signal associated with the cardiac event includes sampling the cardiac signal to generate a number of samples and comparing a selected sample to a sample threshold and, if the sample magnitude does not exceed the sample threshold, replacing the sample with a different value.

17. The ICSD of claim 16, wherein the means for analyzing is configured such that the samples are at least temporarily stored in a form having a least amplitude and a greatest amplitude, wherein, if the sample magnitude does not exceed the sample threshold, the method includes replacing the selected sample with a value corresponding to the least amplitude.

18. The ICSD of claim 16, wherein the means for analyzing is configured such that the stored template includes a number of template samples and, if one or more of the template samples do not exceed the threshold, those template samples are marked, and the selected sample of the portion of the cardiac signal is selected such that it corresponds to a marked sample of the template when the portion of the cardiac signal is compared to the stored template.

19. The ICSD of claim 18, wherein the means for analyzing is configured such that of comparing the conditioned portion of the cardiac signal to the stored template yields a series of comparison values, and of analyzing the portion of the cardiac signal further includes performing a vector multiplication of the series of comparison values with a series of weighting values to yield a set of weighted comparison values and then summing the series of weighted comparison values to generate a value indicative of the degree of correlation of the cardiac signal to the stored template.

20. The ICSD of claim 16, wherein the means for analysis is further configured to apply a weighting factor vector to the samples to give some signal samples greater analytical weight than others.

* * * * *